(12) United States Patent
Xie et al.

(10) Patent No.: US 7,368,631 B2
(45) Date of Patent: *May 6, 2008

(54) **REGENERATION AND GENETIC TRANSFORMATION OF *ACACIA MANGIUM***

(75) Inventors: Deyu Xie, Singapore (SG); Yan Hong, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 329 days.

This patent is subject to a terminal disclaimer.

(21) Appl. No.: 11/007,194

(22) Filed: Dec. 9, 2004

(65) Prior Publication Data

US 2005/0155116 A1    Jul. 14, 2005

Related U.S. Application Data

(62) Division of application No. 09/936,612, filed as application No. PCT/SG00/00010 on Jan. 19, 2000, now Pat. No. 6,846,971.

(51) Int. Cl.
| | |
|---|---|
| *C12N 5/04* | (2006.01) |
| *C12N 5/10* | (2006.01) |
| *C12N 15/82* | (2006.01) |
| *C12N 15/84* | (2006.01) |

(52) U.S. Cl. .................... 800/294; 800/278; 435/410; 435/469; 435/430; 435/431; 435/420; 435/468

(58) Field of Classification Search ............... 800/278, 800/298, 294; 435/468, 469
See application file for complete search history.

(56) References Cited

U.S. PATENT DOCUMENTS 6,846,971 B1 *   1/2005   Xie et al. .................... 800/294

FOREIGN PATENT DOCUMENTS

| JP | 07 255304 A | 9/1995 |
|---|---|---|
| WO | WO 97 23126 | 7/1997 |

OTHER PUBLICATIONS

Hansen et al (1999, Trends in Plant Science 4(6):226-231.*
Galiana, A. et al. In vitro propagation of the nitrogen-fixing tree-legume *Acacia mangium* willd. Plant and Soil, 135(2): 151-159 (1991).
Fakhrai, H, et al., In Vitro Culture and Plant Regeneration in *Vicia faba* subsp. Equina (var. Spring Blaze). *Journal of Experimental Botany*, 40:216, (1989), 813-817, XP-001034860.
Rao, G.V.R., et al., Plantlet Regeneration from the Hypocotyl Callus of *Acacia auriculiformis*—Multipurpose Tree Legume, *J. Plant Physiol.*, 137, (1991), 625-627.
Huetteman, C.A.., et al., Thidiazuron: A potent cytokinin for woody plant tissue culture. *Plant Cell, Tissue and Organ Culture*, 33, (1993) 105-119, XP-000989639.
Rout, G.R. et al., Somatic embryogenesis and plant regeneration from callus culture of *Acacia catechu*—a multipurpose leguminous tree. *Plant Cell, Tissue and Organ Culture*, 42, (1995), 283-285, XP-000989635.
Bhaskar, P., et al., Micropropagation of *Acacia mangium* Willd through nodal bud culture. *Indian Journal of Experimental Biology*, 34, (1996), 590-591, XP-001050518.
Mohamed, M.E., et al., Shoot regeneration from mature endosperm of *Passiflora foetida*. Plant Cell, Tissue and Organ Culture, 46: 161-164, 1996.
Kaur, K., et al., Plants obtained from the Khair tree (*Acacia catechu* Willd.) using mature nodal segments. *Plant Cell Reports*, 17, (1998), 427-429, XP-001034850.
Murthy, B.N.S., et al., Thidiazuron: A potent regulator of In Vitro plant morphogenesis. *In Vitro Cell. Dev. Biol.—Plant*, 34, (1998), 267-275, XP-000989563.
Xie, D., et al., In Vitro regeneration of *Acacia mangium* via organogenesis. *Plant Cell, Tissue and Organ Culture*, 66, (2001), 167-173, XP-001034852.
Hansen, G., et al., Recent advances in the transformation of plants. *Trends in Plant Science*, 4, (1999), 226-231.

* cited by examiner

*Primary Examiner*—Stuart F. Baum
(74) *Attorney, Agent, or Firm*—Rothwell, Figg, Ernst & Manbeck, P.C.

(57) ABSTRACT

The present invention is directed to a method of *Acacia mangium* regeneration through organogenesis and a method of genetic transformation of *Acacia mangium*. The method of regeneration comprises inducing callus from different parts of seedlings and vegetatively micropropagated plantlets as explants; adventitious bud induction followed by pinnate leaf and bud elongation and eventually, elongated shoots were induced to root. Based on the regeneration system, a marker gene GUS under cauliflower mosaic virus promoter was introduced to *Acacia mangium* via *Agrobacterium* infection. GUS staining in the regenerated plants and Southern blot hybridization prove the incorporation of the foreign gene into the host genome and expression of the foreign gene.

5 Claims, 11 Drawing Sheets

A

B

REGENERATION AND GENETIC TRANSFORMATION OF ACACIA MANGIUM

This application is a division of prior, application Ser. No. 09/936,612, which is now U.S. Pat. No. 6,846,971, filed on Jan. 2, 2002, under Section 371 based on application PCT/SG00/00010, filed on Jan. 19, 2000, which is incorporated herein by reference in its entirety.

BACKGROUND OF THE INVENTION

Forests are very important to the world economy and for maintaining and preserving our ecosystem. Forest trees have a wide range of commercial uses (timber for construction, raw material for paper and pulp production, and as an energy source). The global demand for wood products (mostly for paper and pulp and firewood in developing countries) has been increasing year by year when the natural forests are in short supply. Re-forestation is the solution to meeting such increasing demand. Usually, the fast-growing, widely adapted tree species are chosen for re-forestation. Most tree-improvement programs are based on the management of genetic resources, including the selection of superior clones from existing forests, the conservation of genetic variability, partially controlled propagation and classical breeding for desired traits. In spite of the fact that it usually takes several generations to breed, this traditional breeding has been successful in getting elite trees with fast and uniform growth. However, many other traits such as disease and insect resistance, different lignin composition and content are difficult to acquire mainly due to high heterozygosity in tree species and big segregation population. Moreover, the gene(s) conferring certain phenotypes like disease resistance may not be in the gene pool at all. On the other hand, molecular breeding based on genetic transformation of tree species offers the possibility to introduce a particular phenotype without affecting the genetic background of a cultivar. Genetic transformation in *Populus* species and *Eucalyptus* species enabled some success in modification of lignin content (Tzfira et al., 1998; Robinson, 1999). The precondition of molecular breeding of forest tree species is the availability of a reliable and reproducible genetic transformation method, which in turn relies on a system of regeneration of one whole plant from a single cell.

Genus *Acacia* comprises about 1200 tropical and sub-tropical tree species. It belongs to the family *Mimosaceae*. *Acacia mangium* is a multipurpose, fast growing and nitrogen fixing elite tropical legume tree. An adult tree is up to 30-metres tall and its bole (trunk) is often straight to over half the total height. The true leaf of a seedling is a fern-like pinnate leaf. The first pinnate leaf of a seedling has 6 or 8 leaflets, and then the bipinnate leaf develops from the second pinnate leaf on a seedling. Usually when the young seedling grows up to 8-12 bipinnate leaves, the petiole is dilated into a phyllode, while the leaflets abort completely and the true leaf disappears from the young seedling. Phyllodes are flattened leaf stems which look and act like the ordinary leaves of other plants. Branchlets, phyllodes and petioles are glabrous or slightly scurfy. Phyllodes are 5-10 cm broad, 2-4 times as long as broad, dark green, and are chartaceous when dry. The phyllodes have 3-4 longitudinal main nerves which join on the dorsal margin at the base of the phyllode. Secondary nerves are fine and inconspicuous.

Flowers are in loose spikes to 10 cm long and are solitary or paired in the upper axils. Flowers are pentamerous and the calyx is 0.6-0.8 mm long with short obtuse lobes. The corolla is twice as long as the calyx. Pods are linear, glabrous, 3-5 mm broad, about 7.5 cm long when green, woody, coiled and brackish-brown when mature, and depressed between the seeds. Seeds are lustrous, black, ellipsoid, ovate or oblong, 3.5×2.5 mm, with the orangish funicle forming a fleshy aril beneath the seed (Duke, 1984). Due to *A. mangium* fast growth, tolerance of infertile soil and high quality fibre, it has been increasingly used for reforestation plantation and soil rehabilitation in degraded soil. Its plantation has been studied for many years in many countries or regions, especially in tropical regions and subtropical regions, such as Australian, Indonesia, Malaysia, India, Thailand, Hawaii, China and Taiwan. Many *A. mangium* plantations have been established in acidic soil or abandoned land or Imperata grassland, for example, in Bangladesh (Latif et al., 1995); in Sabah (Latif et al., 1995; Williams et al., 1992) and in Serdong (Majid et al., 1994; Awang, 1994) in Malaysia; Sangmelina, Cameroon, Kenya (Duguma et al., 1994); Skaerat, Thailand (Khemnark, 1994); Hawaii, USA (Cole et al., 1996); Bogor (Anwar, 1992; Wibowo et al., 1992), Paseh and Kadipaten (Widiarti and Alrasjid, 1987) in Indonesia; Bengal, India (Basu et al., 1987), etc.

Indonesia, with some of the world's largest paper and pulp mills, has been increasingly relying on plantations as the source of wood and *A. mangium* is the preferred choice. Asia Paper and Pulp group has two affiliate companies with a total concession of 540,000 hectares. By 1996, one company had planted 123,000 hectares of *A. mangium*, about 90% of all its plantation, which represented 180 million seedlings. It is estimated that by 2004, Asia Paper and Pulp group will virtually source all its wood from plantation, mainly *A. mangium* plantation (Bayliss, 1998a; Bayliss, 1998b).

Besides its use for paper and pulp, *A. mangium* timber can be used for other applications such as cement banded particle board, plywood and decorative panel manufacture (Yusoff et al., 1989; Wong et al., 1988).

A large scale of mono-plantation of vegetative propagation from a single plant faces a higher risk of disease infection. It has been found that diseases spread very fast in this kind of plantation and cause large economic losses. Many diseases devastate *A. mangium*: Cinnamon fungus (*Phytophehera cinnamomi*) infection results in collapse and death of plants; Seedling blight, defoliation and dieback due to *Glomerella cingulata* caused serious losses to *A. mangium* in nurseries. Leaf spot by *Cyclindrocladium quinquesep-tatum* causes defoliation of seedlings and young trees; Powdery mildew (*Oidium* spp) severely affected *A. mangium* seedlings in nurseries in Thailand; Red rot diseases, caused by *ganoderma* sp. affects *A. mangium* in Malaysia; Brown root disease caused by *Phellinus noxium* affects *A. mangium* in Malaysia and the Solomon islands (Simmons, 1987; Gutteridge and Shelton, 1994). Traditional breeding has been less successful in getting disease resistance in *A. mangium*, mostly likely due to lack of such a gene in the natural gene pool. Molecular breeding by introducing foreign disease resistance genes becomes an important option.

Studies on *A. mangium* tissue culture have been limited to micropropagation (Bhaskan and Subbash, 1996; Ahmad, 1991; Galiana et al., 1991a; Galiana et al., 1991b). A combination of traditional breeding of elite trees and techniques of large-scale vegetative propagation make the large-scale plantation possible. There has been no report on regeneration or genetic transformation of *A. mangium*. Our invention describes the conditions for regeneration of whole plant via organogenesis and a genetic transformation system.

The publications and other materials used herein to illuminate the background of the invention or provide additional details respecting the practice, are incorporated by reference, and for convenience are respectively grouped in the appended List of References.

SUMMARY OF THE INVENTION

A. System of Regeneration from Callus in *Acacia mangium*

Different parts of *Acacia mangium* seedlings or vegetative micropropagated plantlets (hypocotyl, cotyledon, leaflet, petiole and stem) were used as explants. The seedlings were from isolated seed embryo culture and the plantlets were obtained by micropropagation from meristem regions of a 2-year old tree. Callus formation was induced by MS basic medium (Murashige and Skoog, 1962) supplemented with auxins (either 2,4-D from 0.5 mg/l to 5 mg/l or α-naphthaleneacetic acid (NAA) from 0.5 mg/l to 2 mg/l) and cytokinins (either kinetin (KT) 0.5 mg/l to 3.0 mg/l or 6-benzylaminopurine (6-BA or BA) 0.5 mg/l to 3.0 mg/l).

Adventitious bud induction was achieved on medium AM-265 (MS basic medium with thidiazuron (1-phenyl-3-(1,2,3-thiadiazol-5-yl)urea or TDZ) 1.0 mg/l, indole-3-acetic acid (IAA) 0.25 mg/l, casein enzymatic hydrolysate (CH) 100 mg/l, L-ascorbic acid (vitamin C or Vc) 100 mg/l, L-glutamine (Gln) 150 mg/l, L-asparagine monohydrate (Asn) 150 mg/l, L-proline (Pro) 150 mg/l, pH 5.8 after autoclaving, phytagel 0.275 or 0.30%, or agar 0.8%, sucrose 30 g/L) under the growth conditions of 16/8 hours light/dark (L/D) cycle and at 28° C.

Pinnate leaf formation and adventitious bud elongation were obtained on medium AM-337 (MS basic medium with TDZ 0.01 mg/l, CH 100 mg/l, Vc 100 mg/l, Gln 150 mg/l, Asn 150 mg/l and Pro 150 mg/l, pH 5.8 after autoclaving, phytagel 0.275 or 0.30%, or agar 0.8%, sucrose 30 g/L), or AM-41 (MS basic medium supplemented with 6-BA 2 mg/l, CH 100 mg/l, Vc 100 mg/l, Gln 150 mg/l, Asn 150 mg/l and Pro 150 mg/l, pH 5.8 after autoclaving, phytagel 0.275 or 0.30%, or agar 0.8%, sucrose 30 g/L) supplemented with gibberellic acid ($GA_3$) 0.5-2.5 mg/l. The growth conditions are 16/8 hrs (L/D) cycle and at 28° C.

Adventitious buds formed roots and complete plantlets were obtained on MS or ½ MS basic medium supplemented with NAA 0.5 to 3.0 mg/l combined with KT 0-0.5 mg/l or IBA (indole butyric acid) 0.01-0.5 mg/l and CH 100 mg/l, Vc 100 mg/l, Gln 150 mg/l, Asn 150 mg/l and Pro 150 mg/l, pH 5.8 after autoclaving, phytagel 0.35%, or agar 1.4%, sucrose 20 or 30 g/L under the growth conditions of 16/8 hrs (L/D) cycle and at 28° C. Complete plantlets were transplanted into peat soil: white sand (3:1) in a growth chamber at a photoperiod of 16/8 hrs (L/D) and 25° C.

B. System of Genetic Transformation of *A. mangium*

Based on the above established regeneration system, *Agrobacterium* strain LBA4404 (Ooms et al., 1981) harbouring binary vector pBI121 in which a GUS gene is under regulation of an 800 bp cauliflower mosaic virus promoter was used for genetic transformation of *A. mangium*. The *Agrobacteria* with the plasmid were co-cultured with the following explants: (1) Young adventitious shoots vegetatively micropropagated from auxiliary buds dissected from a 2-year old tree. The shoots consisted of young stem and pinnate leaves but no phyllodes. Stem pieces of about 2-3 cm in length after separating pinnate leaf and auxiliary buds were used as explants. (2) Petiole pieces of 1-2 cm in length and leaflet pieces of 0.4-0.5×0.3-0.4 (cm) from seedlings derived from embryo culture were used as explants. The explants were pre-cultured on AM-265 for three days at 16/8 hrs (L/D) cycle and at 28° C. before infection with activated *Agrobacterium* for 15 minutes. Infected explants were then cultured for 3 days in the same media in the dark at 22° C. They were then washed and put into AM-265 to induce callus and adventitious buds. Transgenic plants were selected with G418 in media in four stages: G418 12 mg/l for 25 days, G418 20 mg/l for 60 days, G418 30 mg/l for 25 days and then on G418 12 mg/l. Adventitious bud elongation was induced by AM-265 with $GA_3$ 2.5 to 5 mg/l in the presence of G418 12 mg/l. For pinnate leaf formation, adventitious buds were transferred into AM-41 with $GA_3$ 2.5 mg/l at growth conditions of 16/8 hours (L/D) cycle and 28° C. Regenerated shoots were excised and checked for GUS staining and 16% tested positive. Putative transgenic adventitious buds were transferred into AM-357 or AM-451 with or without G418 (10 mg/l) at the photoperiod of 16/8 hours (L/D) to induce rooting. Southern blot hybridization showed positive results when NPTII gene was used as probe.

BRIEF DESCRIPTION OF THE FIGURES

FIG. 1A shows callus induction. FIG. 1B shows adventitious bud recovery. FIGS. 1C, 1D and 1E show plumule formation and adventitious bud elongation.

FIG. 2C shows callus induction. FIG. 2B shows adventitious bud recovery. FIG. 2C shows plumule formation and adventitious bud elongation.

FIG. 3A shows regeneration from callus. FIG. 3B shows adventitious buds induced from callus. FIG. 3C show root formation, FIG. 3D shows a complete plantlet and FIG. 3E shows a one month old plantlet in pot soil.

FIG. 5A shows a two-year old tree. FIG. 5B shows adventitious bud induction. FIG. 5C shows propagated adventitious buds with plumules.

FIGS. 9A-B show stem pieces and FIG. 9C shows a shoot.

DETAILED DESCRIPTION OF THE INVENTION

Figure 1:
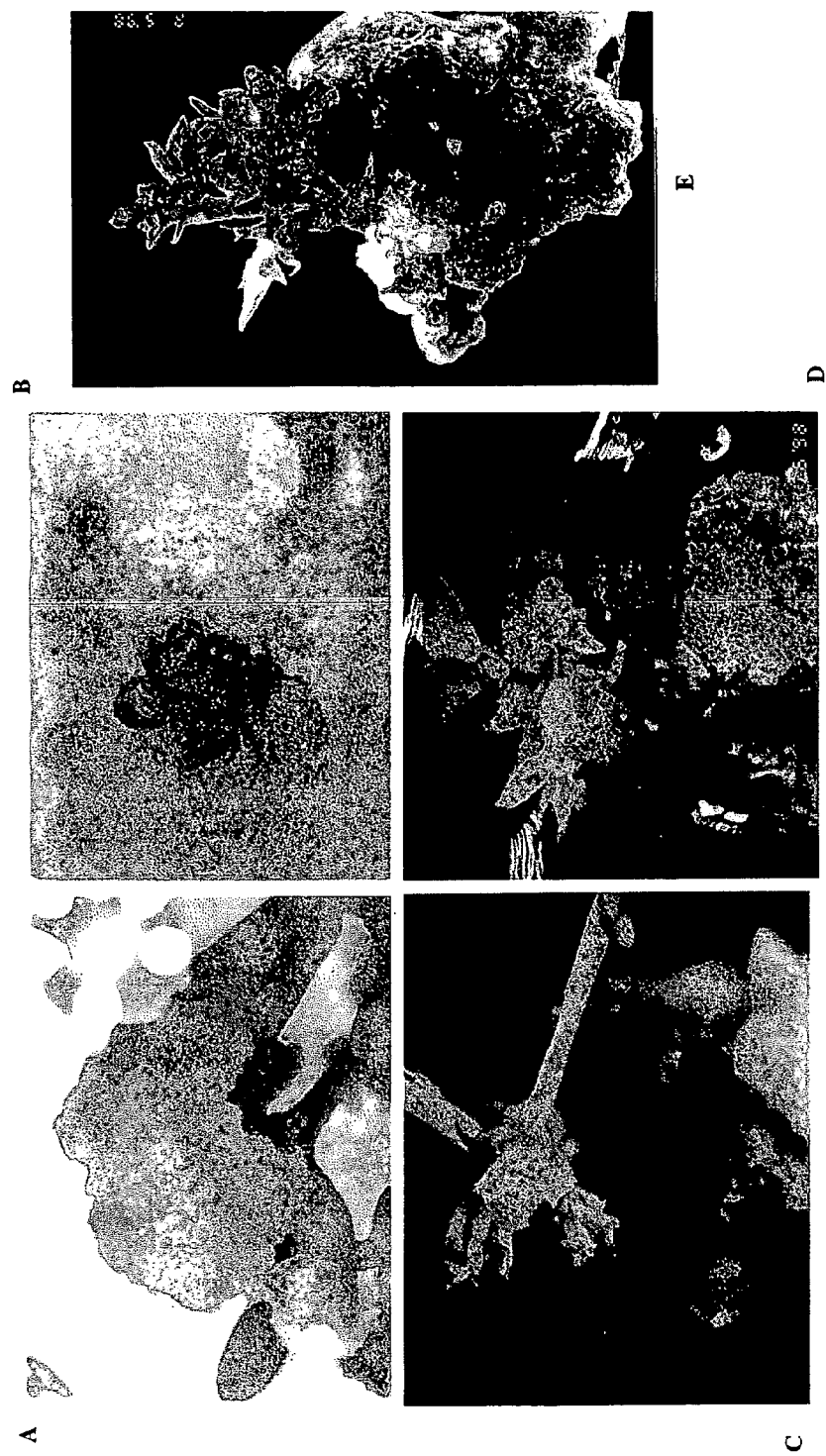
FIGS. 1A-E show adventitious bud induction from leaf.

The present invention is directed to methods for genetically transforming tissue of trees, especially *Acacia mangium*, and regenerating whole plants via organogenesis from the transformed tissue.

The present invention is further detailed in the following Examples, which are offered by way of illustration and are not intended to limit the invention in any manner. Standard techniques well known in the art or the techniques specifically described below are utilized.

EXAMPLE 1

Reagents and Culture Media

A. MS Basic Medium: MS Medium (Murashige and Skoog, 1962)

| Name | Molecular formula | Concentration (mg/l) | Sigma Cat. No. |
|---|---|---|---|
| Macronutrients | | | |
| Ammonium Nitrate | $NH_4NO_3$ | 1,650 | A-3795 |
| Potassium Nitrate | $KNO_3$ | 1,900 | P-8291 |
| Calcium Chloride dihydrate | $CaCl_2 \cdot 2H_2O$ | 440 | C-2536 |
| Magnesium Sulfate Heptahydrate | $MgSO_4 \cdot 7H_2O$ | 370 | —7774 |
| Potassium phosphate monobasic, anhydrous | $KH_2PO_4$ | 170 | P-8416 |
| Ferrous Sulfate Heptahydrate | $FeSO_4 \cdot 7H_2O$ | 27.8 | F-8263 |
| Ethylenediaminetetraacetic acid (EDTA) | $C_{10}H_{14}N_2O_8Na_2 \cdot 2H_2O$ ($Na_2EDTA$) | 37.3 | E-6635 |
| Micronutrients | | | |
| Potassium Iodide | KI | 0.83 | P-8166 |
| Boric Acid | $H_3BO_3$ | 6.2 | B-9645 |
| Manganese Sulfate monohydrate | $MnSO_4 \cdot H_2O$ | 16.9 | —7899 |
| Zinc Sulfate | $ZnSO_4 \cdot 7H_2O$ | 8.6 | Z-1001 |
| Molybdic Acid (Sodium salt:dihydrate) | $Na_2MoO_4 \cdot 2H_2O$ | 0.25 | —1651 |
| Cupric Sulfate (Pentahydrate) | $CuSO_4 \cdot 5H_2O$ | 0.025 | C-3036 |
| Cobalt Chloride (hexahydrate) | $CoCl_2 \cdot 6H_2O$ | 0.025 | C-2911 |
| Organic Reagents | | | |
| myo-Inositol | $C_6H_{12}O_6$ | 100 | I-3011 |
| Nicotinic acid | $C_6H_5NO_2$ | 0.5 | —0765 |
| Glycine | $C_2H_5NO_2$ | 2.0 | G-6143 |
| Thiamine (Vitamin B1) | $C_{12}H_{17}ClN_4OS \cdot HCl$ | 0.1 | T-3902 |
| Pyridoxine (Vitamin B6) Hydrochloride | $C_8H_{11}NO_3 \cdot HCl$ | 0.5 | P-9755 |

B. Other Organic Reagents

| Name | Molecular formula | Sigma Cat. No. |
|---|---|---|
| L-Ascorbic acid (Vitamin C) | $C_6H_8O_6$ | A-2174 |
| Casein Enzymatic Hydrolysate (CH) | | C-7290 |
| L-Glutamine (Gln) | $C_5H_{10}N_2O_3$ | G-9273 |
| L-Asparagine monohydrate (Asn) | $C_4H_8N_2O_3 \cdot H_2O$ | A-4284 |
| L-Proline (Pro) | $C_5H_9NO_2$ | P-4655 |
| Sucrose | | S-5390 |

C. Plant Growth Regulators

| Name | Sigma Cat. No. |
|---|---|
| Indole-3-acetic Acid (IAA) | I-2886 |
| α-Naphthaleneacetic Acid (NAA) | —0640 |
| 1-Phenyl-3-(1,2,3-thiadiazol-5-yl)Urea (Thidiazuron, TDZ) | P-6186 |
| 6-Benzylaminopurine (6-BA) | B-3408 |
| Kinetin (KT) | K-0753 |
| Gibberellic Acid ($GA_3$) | G-7645 |

D. Agar

| Name | Sigma Cat. No. |
|---|---|
| Type M | A-4800 |
| Purified | A-7921 |
| Phytagel | P-8169 |

E. Antibiotics

| | |
|---|---|
| Timentin (T) | Beecham Pharmaceuticals (Pte) Ltd |
| Kanamycin (K) | Sigma |
| Genetins (G418 Sulfate) | Clontech 8056-2 |

F. Media for Callus Induction

| | |
|---|---|
| AM-5 | MS + 2,4-D 2.0 mg/l + KT 3.0 mg/l |
| AM-6 | MS + 2,4-D 2.0 mg/l + KT 0.5 mg/l |
| AM-7 | MS + NAA 2.0 mg/l + KT 3.0 mg/l |
| AM-8 | MS + NAA 2.0 mg/l + KT 0.5 mg/l |
| AM-14 | MS + 2,4-D 0.5 mg/l + 6-BA 3.0 mg/l |
| AM-15 | MS + 2,4-D 1.0 mg/l + 6-BA 3.0 mg/l |
| AM-16 | MS + 2,4-D 2.0 mg/l + 6-BA 3.0 mg/l |
| AM-17 | MS + 2,4-D 0.5 mg/l + 6-BA 0.5 mg/l |
| AM-18 | MS + 2,4-D 1.0 mg/l + 6-BA 0.5 mg/l |
| AM-19 | MS + 2,4-D 2.0 mg/l + 6-BA 0.5 mg/l |
| AM-20 | MS + 2,4-D 0.5 mg/l + 6-BA 1.0 mg/l |
| AM-21 | MS + 2,4-D 1.0 mg/l + 6-BA 1.0 mg/l |
| AM-22 | MS + 2,4-D 2.0 mg/l + 6-BA 1.0 mg/l |
| AM-27 | MS + NAA 0.5 mg/l + 6-BA 3.0 mg/l |
| AM-28 | MS + NAA 1.0 mg/l + 6-BA 3.0 mg/l |
| AM-29 | MS + NAA 2.0 mg/l + 6-BA 3.0 mg/l |
| AM-30 | MS + NAA 0.5 mg/l + 6-BA 0.5 mg/l |
| AM-31 | MS + NAA 1.0 mg/l + 6-BA 0.5 mg/l |
| AM-32 | MS + NAA 2.0 mg/l + 6-BA 0.5 mg/l |
| AM-33 | MS + NAA 0.5 mg/l + 6-BA 1.0 mg/l |
| AM-34 | MS + NAA 1.0 mg/l + 6-BA 1.0 mg/l |
| AM-35 | MS + NAA 2.0 mg/l + 6-BA 1.0 mg/l |
| AM-231 | MS + 2,4-D 5.0 mg/l + KT 0.5 mg/l |
| AM-233 | MS + 2,4-D 0.5 mg/l + KT 1.0 mg/l |
| AM-234 | MS + 2,4-D 1.0 mg/l + KT 1.0 mg/l |

G. Media for Adventitious Buds Induction
a. AM-265: MS basic medium with TDZ 1.0 mg/l, IAA 0.25 mg/l, CH 100 mg/l, Vc 100 mg/l, Gln 150 mg/l, Asn 150 mg/l and Pro 150 mg/l, pH 5.8 after autoclaving, phytagel 0.275 or 0.30%, or agar 0.8% (A-4800, Sigma), sucrose 30 g/L.
b. AM-261: MS basic medium with TDZ 1.0 mg/l, IAA 0.5 mg/l, CH 100 mg/l, Vc 100 mg/l, Gln 150 mg/l, Asn 150 mg/l, Pro 150 mg/l, pH 5.8 after autoclave, phytagel 0.275 or 0.30%, or agar 0.8% (A-4800, Sigma), sucrose 30 g/L.
c. AM-304: MS basic medium with TDZ 2.0 mg/l, IAA 0.25 mg/l, CH 100 mg/l, Vc 100 mg/l, Gln 150 mg/l, Asn 150 mg/l and Pro 150 mg/l, pH 5.8 after autoclave, phytagel 0.275 or 0.30%, or agar 0.8% (A-4800, Sigma), sucrose 30 g/L.
d. AM-308: MS basic medium with TDZ 1.0 mg/l, IAA 2.0 mg/l, CH 100 mg/l, Vc 100 mg/l, Gln 150 mg/l, Asn 150 mg/l and Pro 150 mg/l, pH 5.8 after autoclaving, phytagel 0.275 or 0.30%, or agar 0.8% (A-4800, Sigma), sucrose 30 g/L.

H. Media for Pinnate Leaf Formation
a. AM-337: MS basic medium with TDZ 0.01 mg/l, CH 100 mg/l, Vc 100 mg/l, Gln 150 mg/l, Asn 150 mg/l and Pro 150 mg/l, pH 5.8 after autoclaving, phytagel 0.275 or 0.30%, or agar 0.8% (A-4800, Sigma), sucrose 30 g/L.
b. AM-4 1: MS basic medium supplemented with 6-BA 2 mg/l, CH 100 mg/l, Vc 100 mg/l, Gln 150 mg/l, Asn 150 mg/l and Pro 150 mg/l, pH 5.8 after autoclaving, phytagel 0.275 or 0.30%, or agar 0.8%, sucrose 30 g/L.

I. Media for Root Formation
a. Modified AM-8: MS basic medium with NAA 2.0 mg/l, KT 0.5 mg/l, CH100 mg/l, Vc 100 mg/l, Gln 150 mg/l, Asn 150 mg/l and Pro 150 mg/l, pH 5.8 after autoclaving, phytagel 0.30%, sucrose 30 g/L.
b. AM-357: ½ MS basic medium with NAA 2.0 mg/l, KT 0.5 mg/l, CH 100 mg/l, Vc 100mg/l, Gln 150 mg/l, Asn 150 mg/l and Pro 150 mg/l, pH 5.8 after autoclaving, phytagel 0.30%, sucrose 30 g/L.
c. AM-451: ½ MS basic medium with NAA 2.0 mg/l, KT 0.1 mg/l, CH 100 mg/l, Vc 100 mg/l, Gln 150 mg/l, Asn 150 mg/l and Pro 150 mg/l, pH 5.8 after autoclaving, phytagel 0.35%, sucrose 20 g/L.

J. Transplantation
Peat soil: white sand 3:1

K. Media for *Agrobacterium tumefaciens* Activation

| LB medium | |
|---|---|
| Tryptone | 1.0% |
| Yeast extract | 0.5% |
| NaCl | 0.8% |
| pH 7.0 before autoclaving | |
| (Sambrook et al., 1989) | |
| YEP medium (Per liter) (Chilton et al., 1974) | |
| Bactopeptone | 10 g |
| Yeast extract | 10 g |
| NaCl | 5 g |
| AB medium | |
| 20 × Phosphate Buffer (per liter) | |
| $K_2HPO_4$ | 60 g |
| $NaH_2PO_4$ | 20 g |
| Autoclave this solution separately | |
| 20 × Salts solution (per liter) | |
| $NH_4Cl$ | 20 g |
| $MgSO_4 \cdot 7H_2O$ | 6 g |
| KCl | 3 g |
| $CaCl_2$ | 0.2 g |
| $FeSO_4 \cdot 7H_2O$ | 0.05 g |
| pH to 7.0 before autoclaving | |
| To make up the final medium, combine | |
| (to a final volume of 1 liter): | |
| 50 ml 20 × Phosphate Buffer | |
| 50 ml 20 × Salts Solution | |
| 900 ml sterile $ddH_2O$ | |
| Induction medium | |
| MES buffer, pH 6.0 | 30 mM |
| 1 × AB medium | |
| Glucose | 0.5% |
| Acetosyringone | 100 µM (a stock solution of acetosyringone must be made up fresh in DMSO) |

EXAMPLE 2

Assay for GUS Activity

Figure 8:
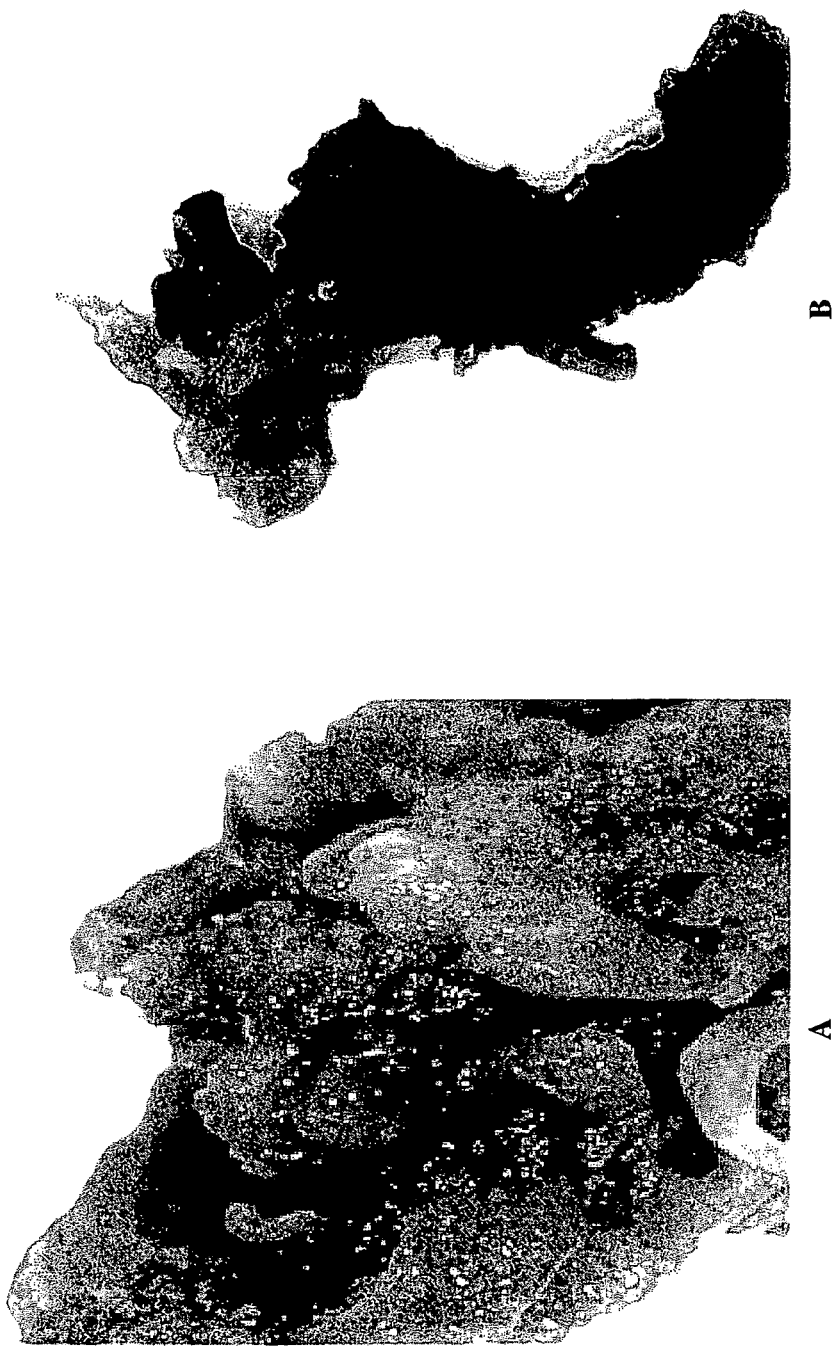
FIGS. 8A and 8B illustrate GUS staining of adventitious buds after selection for 5 months.
Figure 9:
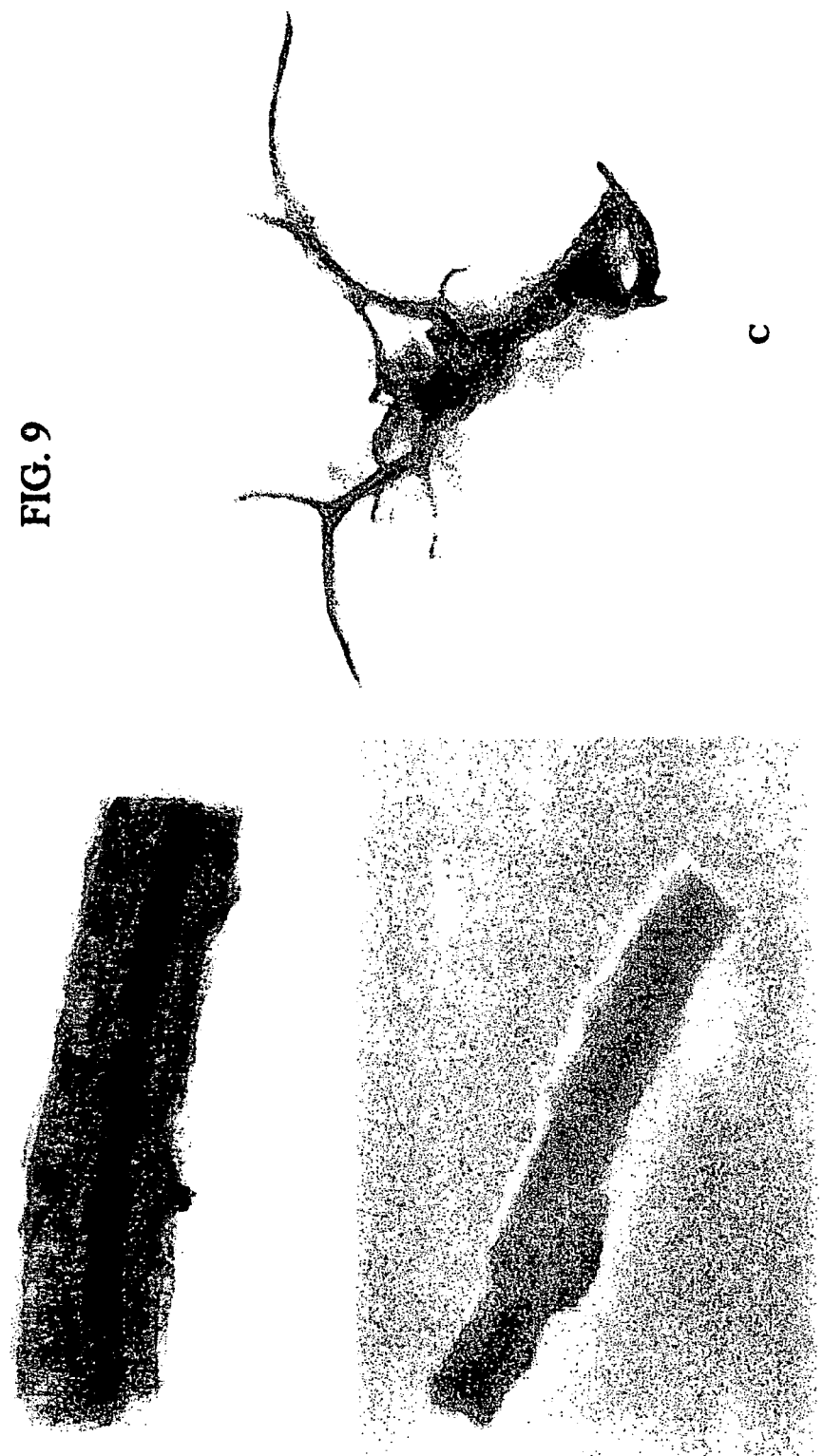
FIGS. 9A-C illustrate GUS staining of young transgenic stem pieces.
Figure 10:
FIGS. 10A-C show GUS staining of transgenic leaf and leaf pieces.

Stain the tissue overnight at 37° C. in GUS staining solution. Gus staining solution is described by Jefferson (1987). It is X-gluc—1 mM, sodium phosphate (pH 7.0)—100 mM, EDTA—10 mM, and Triton X-100—0.1%. GUS staining showed a positive blue reaction in adventitious buds and stem and leaf (FIGS. 8, 9, and 10).

EXAMPLE 3

Southern Analysis

A method for performing Southern blots is described in Sambrook et al. (1989). The method is:

A. DNA Extraction 2-5 g fresh sample was frozen in liquid $N_2$. This was ground with a mortar and pestle in liquid nitrogen to a fine powder. The powder was transferred to a centrifuge tube (50 ml). 15 ml of Extraction Buffer was added, 2 ml 10% SDS was added and mixed thoroughly. This was incubated at 65° C. for 15 minutes. 5 ml 5 M KAc was added and shaken vigorously. The mixture was incubated in ice for 20 minutes and then spun at 25,000× g for 20 minutes. The supernatant was filtered through Microcloth into a new tube. The DNA was precipitated with ½ volume of isopropanol, mixed and incubated at −20° C. for 30 minutes.

The DNA was pelleted at 25,000× g for 30 minutes, the supernatant was poured off, and the tube was inverted and air dried for 30 minutes. The pellet was dissolved with 0.7 ml of 1× TE (pH 8.0) and transferred to an Eppendorf tube. This was spun 10 minutes. The supernatant was transferred to a new tube, 7 µl RNase (10 mg/ml) was added and left at room temperature for 10 minutes, then 75 µl 3 M NaAc (pH 5.3) and 500 µl of isopropanol were added. The solution was mixed and the DNA was pelleted in a microcentrifuge at full speed for 5 minutes. The pellet was washed with 70% ethanol, air dried and dissolved with 100 µl 1× TE (pH 8.0).

B. Extraction Buffer

| 100 mM Tris-HCl, pH 8 | 50 ml |
|---|---|
| 50 mM EDTA, pH 8 | 50 ml |
| 500 mM NaCl | 50 ml |
| 10 mM β-ME | 0.6 ml |
| ddH$_2$O | to 500 ml |

C. Enzyme Digestion

Reaction system I: DNA sample 100 μl (20 μg), 10× HindIII buffer 40 μl, HindIII 8 μl (80 units), add sterile double distilled H$_2$O 252 μl to total volume 400 μl.

The reaction was incubated at 37° C. for overnight. 40 μl of 3 M NaAc (pH 5.3) and ⅔ volume of 100% ethanol were added to the reaction system and this was incubated at −20° C. for 30 minutes. This was spun at full speed at 4° C. for 20 minutes. The supernatant was poured off and the tube was air dried for 30 minutes then the pellet was dissolved in 30 μl sterile double distilled water.

D. Electrophoresis

Electrophoresis was performed on a 0.8% agarose gel in 1× TBE at 28V for overnight.

E. Transfer of DNA from Agarose Gels to Nylon Membranes

This step was performed as described in Sambrook et al. (1989).

F. Prehybridization

A prehybridization solution of 6× SSC, 5× Denhardt's reagent, 0.5% SDS, 100 μg/ml denatured, fragmented salmon sperm DNA (Stratagene products) and 50% formamide was prepared. 50× Denhardt's is: 5 g of Ficoll, 5 g of polyvinylpyrrolidone, 5g of bovine serum albumin and ddH$_2$O to 500 ml, filtered and stored at −20° C.

After fixing DNA to the membrane, the membrane was placed into a hybridization tube containing suitable prehybridization solution using 0.2 ml prehybridization solution for each square centimeter of nylon membrane. The membrane was incubated at 42° C. for 6 hours.

G. Probe Label

During the prehybridization, labeled probe was prepared using a Boehringer Mannheim-High Primer DNA Labeling Kit. 50 ng of NPTII were added then brought to a volume of 8 μl with H$_2$O. The DNA was denatured in a 100° C. heat block for 10 minutes, chilled quickly in ice, and pulse spun.

On ice the denatured DNA was mixed with: 4 μl High Prime reaction mixture, 3 μl of dATP, dGTP, dTTP mixture, and 5 μl of α-$^{32}$P dCTP, 3000 Ci/mmol (Biolab). This was incubated at 37° C. for 10 minutes. The reaction was stopped by adding 20 μl of 50 mM EDTA (pH 8.0).

The labeled probe was purified by running through a small Sephadex G50 column prepared on a small Pasteur pipette. The eluent was monitored with a counter and the first peak was collected.

H. Hybridization

The probe was added into the hybridization tube, then incubated at 42° C. for 10-24 hours.

I. Washing Membrane

The hybridization solution was poured off and the membrane was submerged in 2× SSC, 0.5% SDS at room temperature for 10 minutes. The membrane was transferred into 2× SSC, 0.1% SDS at room temperature for 15 minutes. The solution was replaced with 0.5× SSC, 0.1% SDS and the membrane was incubated at room temperature for 15 minutes. The solution was replaced with 0.1× SSC, 0.1% SDS and incubation continued at 55° C. for 30-55 minutes. The membrane was transferred into 0.1 × SSC at room temperature for 3-5 minutes, then air dried on 3MM Whatman paper for 30 minutes.

J. Autoradiography

The membrane was exposed to X-ray film (Kodak) to obtain an autoradiographic image at −80° C. for one day or more.

Figure 11:
FIG. 11 shows the results of a Southern blot to a NPTII probe. 20 μg of DNA was digested with HindIII, run on a gel and blotted. Lanes 1-6 are transgenic lines. Lane ck is a negative control using DNA from a non-transgenic plant. Lane 7 is a positive control using DNA from a tomato transgenic line by plasmid pWS42 with NPTII as the selection marker.

Using NPTII fragment as a probe, Southern blotting showed that the NPTII gene had integrated in adventitious buds (FIG. 11). The results demonstrate that this protocol of Acacia mangium transformation is very successful.

EXAMPLE 4

Regeneration of A. mangium

A. Embryo Culture

Mature seeds (black coat) were pre-treated with 98% H$_2$SO$_4$ for 2-3 minutes and washed with tap water several times. Treated seeds were sterilized with 70% ethanol for 2-3 minutes and washed times with sterile ddH$_2$O. Seeds were then immersed in 0.1% HgCl$_2$ for 6 minutes and washed 5 times with sterile ddH$_2$O, again sterilized with bleach 30% (market product) for 6 minutes, then washed 5 times with sterile ddH$_2$O. Sterilized seeds were soaked in sterile ddH$_2$O overnight for isolating zygotes for embryo culture. MS basic medium (Murashige and Skoog, 1962), pH 5.8, sucrose 30 g/L, phytagel 0.25% or agar 0.7% (Sigma, A-4800), with or without activated charcoal, was used to culture mature embryo. Isolated mature zygotic embryos were cultured on MS using a photoperiod of 12/12 hours or 16/8 hours (L/D) or complete dark, at 25-28° C. Germinated hypocotyls or leaves or petioles or stems were used as explants to induce callus formation.

B. Callus Induction

Figure 2:
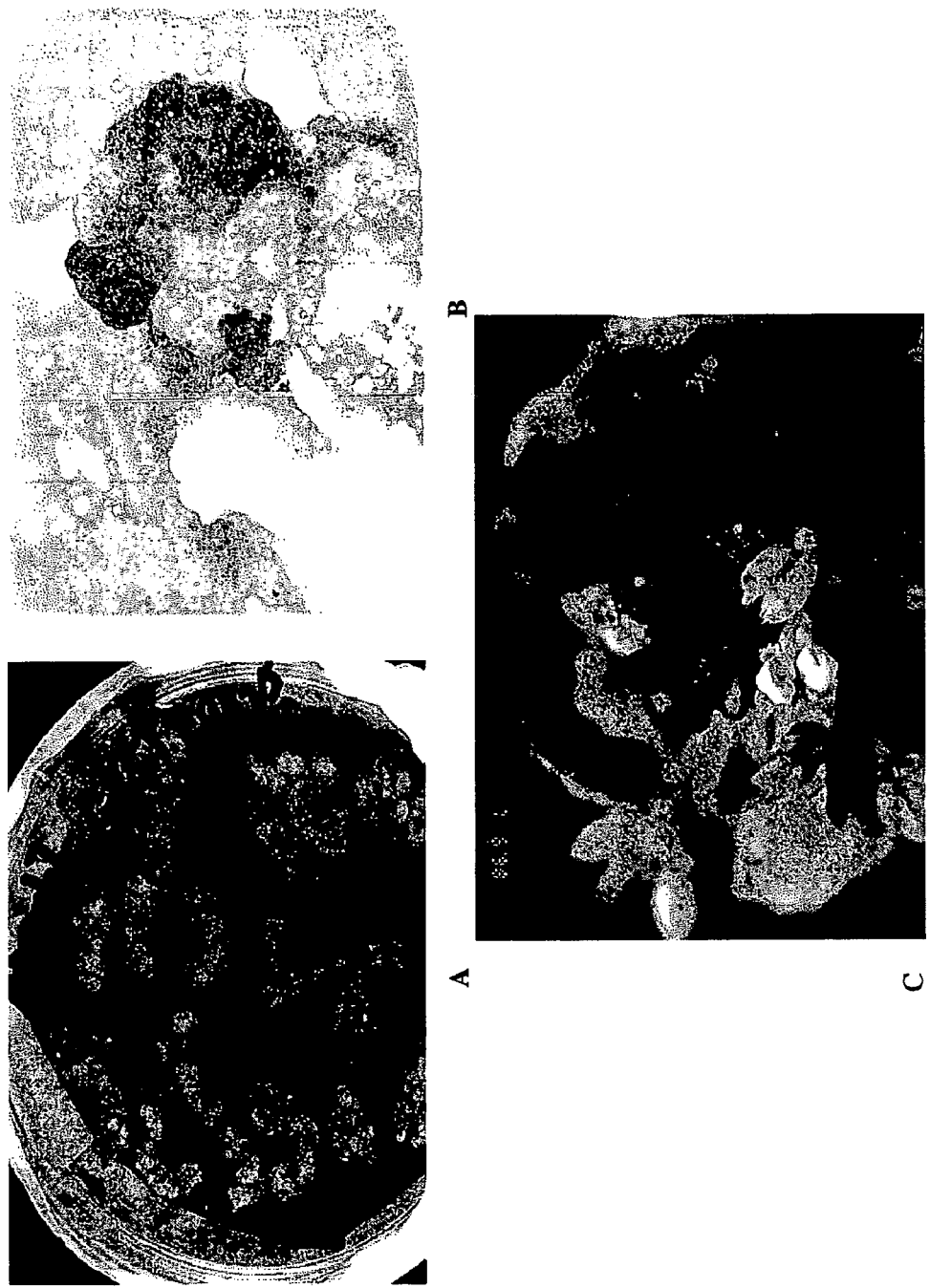
FIGS. 2A-C show *Acacia mangium* regeneration from petiole.
Figure 3:
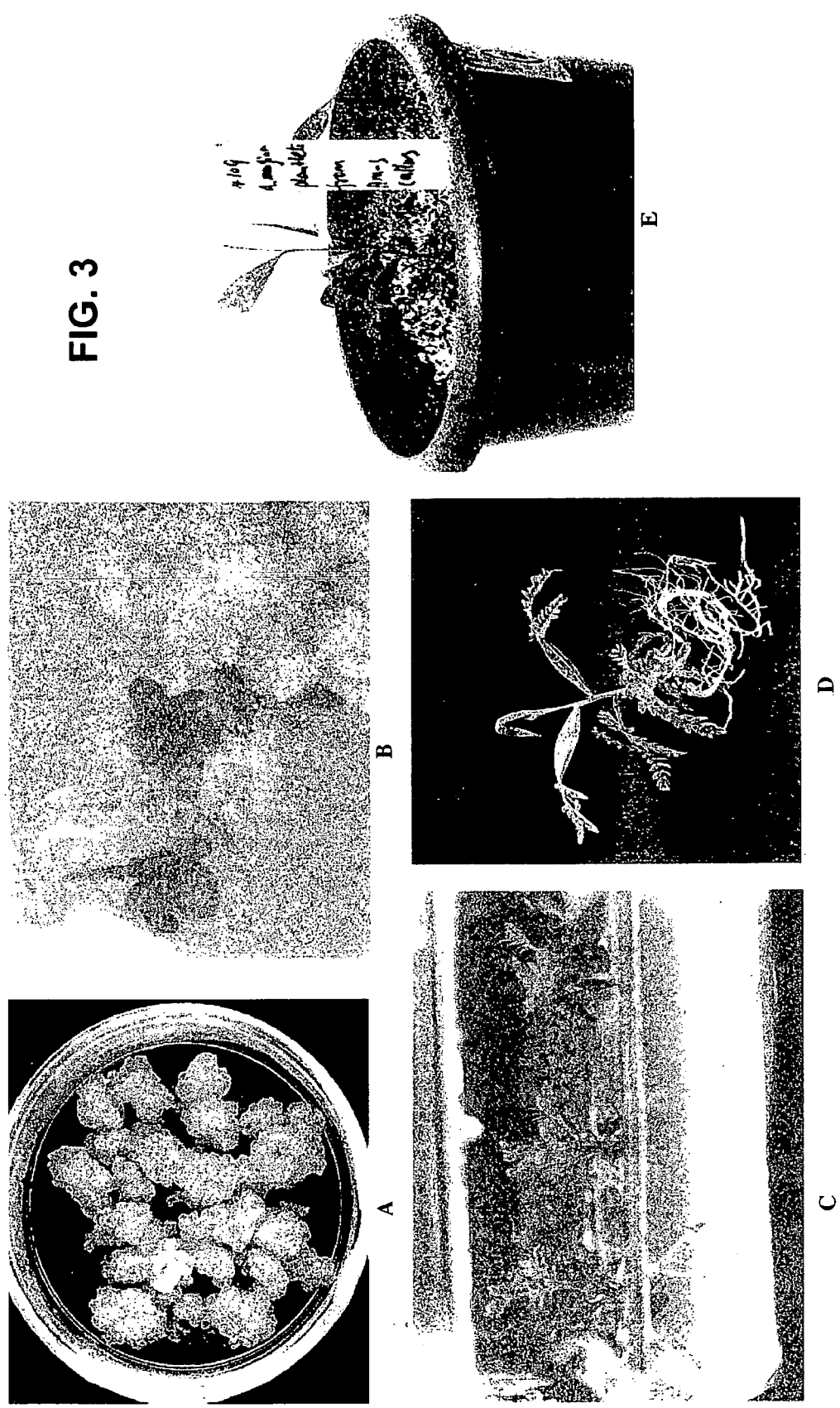
FIGS. 3A-E demonstrate *Acacia mangium* regeneration from stem pieces.

Different media were used to induce callus, including medium Nos. AM-5, 6, 7, 8, 14, 15, 16, 17, 18, 19, 20, 21, 22, 27, 28, 29, 30, 31, 32, 33, 34, 35, 231, 233 and 234 at 12/12 hours or 16/8 hours (L/D) or Dark at 25° C. Callus induced from young leaflet: AM-L; from young petiole: AM-P; from hypocotyl: AM-H; from young stem: AM-S; from bud: AM-B; from root: AM-R. All above calli were used to induce adventitious buds, using a photoperiod of 16/8 hours, 1800-2000 lux, and 28° C. The results of callus induction on different media were different (Table. 1). Generally callus induction was not difficult. All explants produced calli at the photoperiod of 12/12 hrs or 16/8 hrs (L/D) (see, e.g., FIG. 1A; FIG. 2A; FIG. 3A), and 25° C. for 20 days.

TABLE 1

Results of callus induction on different media at 12/12 hours (L/D), 25° C. cultured for 35 days

| Medium No. | Number of Explants (leaflet) | No. of explants forming callus | No. of explants complete callus formation |
|---|---|---|---|
| AM-5 | 40 | 40 | 33 |
| AM-6 | 40 | 40 | 31 |
| AM-7 | 40 | 40 | 3 |
| AM-8 | 40 | 40 | 4 |
| AM-14 | 40 | 40 | 36 |
| AM-15 | 40 | 40 | 40 |

TABLE 1-continued

Results of callus induction on different media at 12/12 hours (L/D), 25° C. cultured for 35 days

| Medium No. | Number of Explants (leaflet) | No. of explants forming callus | No. of explants complete callus formation |
|---|---|---|---|
| AM-16 | 40 | 40 | 38 |
| AM-17 | 40 | 40 | 36 |
| AM-18 | 40 | 40 | 39 |
| AM-19 | 40 | 40 | 39 |
| AM-20 | 40 | 40 | 38 |
| AM-21 | 40 | 40 | 40 |
| AM-22 | 40 | 40 | 40 |
| AM-27 | 40 | 40 | 12 |
| AM-28 | 40 | 40 | 8 |
| AM-29 | 40 | 40 | 11 |
| AM-30 | 40 | 40 | 10 |
| AM-31 | 40 | 40 | 6 |
| AM-32 | 40 | 40 | 2 |
| AM-33 | 40 | 40 | 4 |
| AM-34 | 40 | 40 | 4 |
| AM-35 | 40 | 40 | 6 |
| AM-231 | 40 | 40 | 30 |
| AM-233 | 40 | 40 | 20 |
| AM-234 | 40 | 40 | 20 |
| Petiole | | | |
| AM-6 | 20 | 20 | 15 |
| AM-17 | 20 | 20 | 20 |

C. Adventitious Bud Induction

Calli induced from leaflet, petiole, young stem and buds were cultured on AM-261, AM-265, AM-304, and AM-308, at a photoperiod of 16/8 hrs (L/D), at 28° C. One month later, there were some bud recoveries from callus (FIG. 1B; FIG. 2B). Bud recovery from friable callus first appeared as compact and smooth bud terminal. The ratio of bud recovery reaches 15% on AM-265. But on these media, induced buds could not easily form pinnate leaves and elongate.

D. Pinnate Leaf Formation and Adventitious Bud Elongation

Bud recoveries from callus were transferred into AM-337 or AM-41 with $GA_3$ 2.5 mg/l, at a photoperiod of 16/8 hrs (L/D), 1800-2000 lux, and 28° C. After culture for one month, some of them could form pinnate leaves and elongate (FIGS. 1C, D, E; FIG. 2C; and FIG. 3B). The ratio of pinnate leaf formation and bud elongation reaches 16.67%.

E. Root Formation

Elongated buds were cultured in AM-357 or AM-451 for root formation. 20 days later, adventitious roots began to appear from basic stem of buds (FIG. 3C). After root formation, plantlets were transferred to MS basic medium without any plant growth regulators. Plantlets grow normally and fast, and the root system grew well (FIG. 3D).

F. Transplantation

Phytagel on plantlets was washed away and the plantlets were transferred to pot (peat soil: white sand 3:1) and grown in a growth chamber at a photoperiod of 16/8 hours and 25° C. One month later the plantlets were transferred to a green house (FIG. 3E).

EXAMPLE 5

Rejuvenation of Tree

Figure 5:
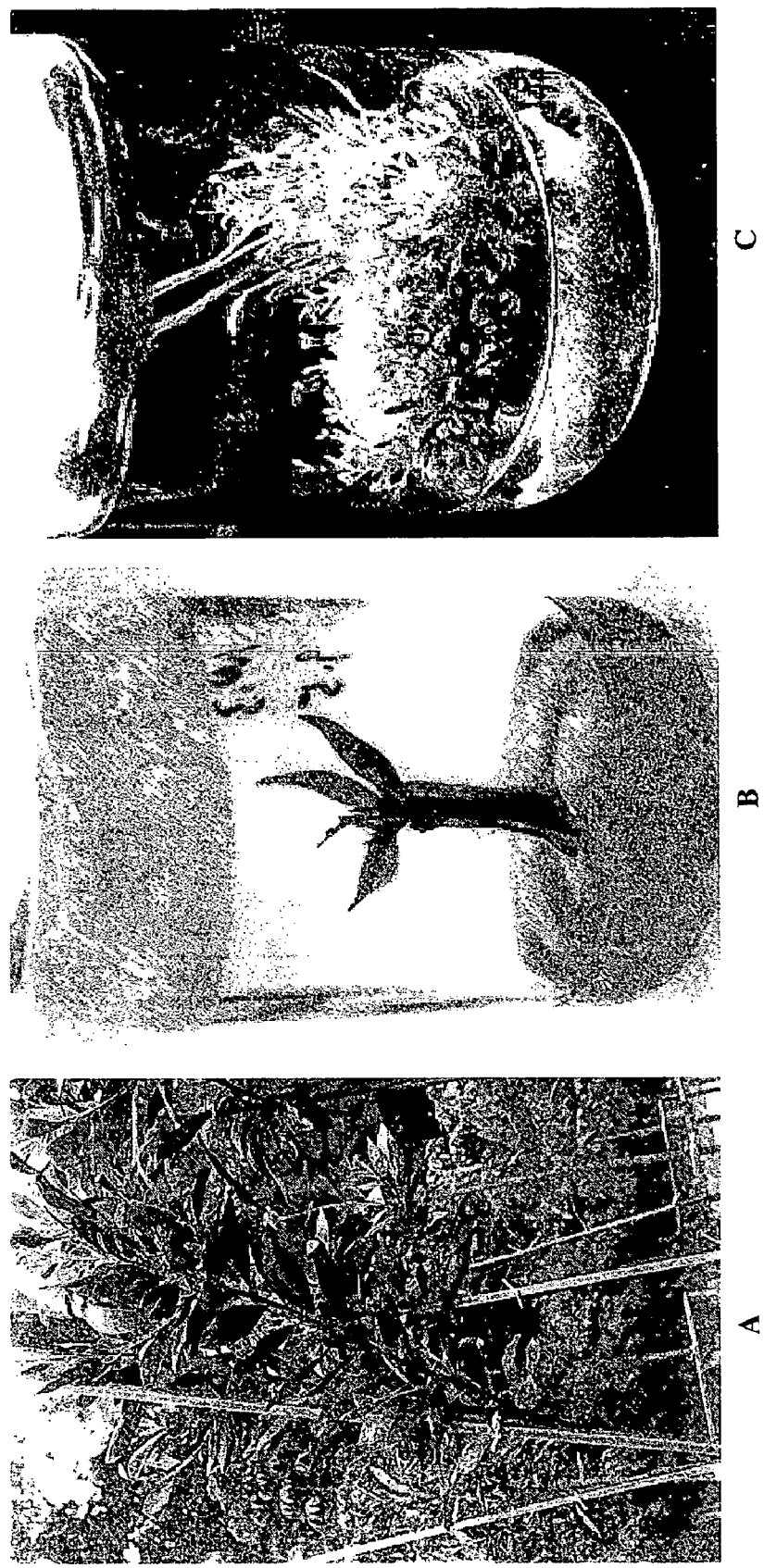
FIGS. 5A-C demonstrate rejuvenation of a tree.
Figure 6:
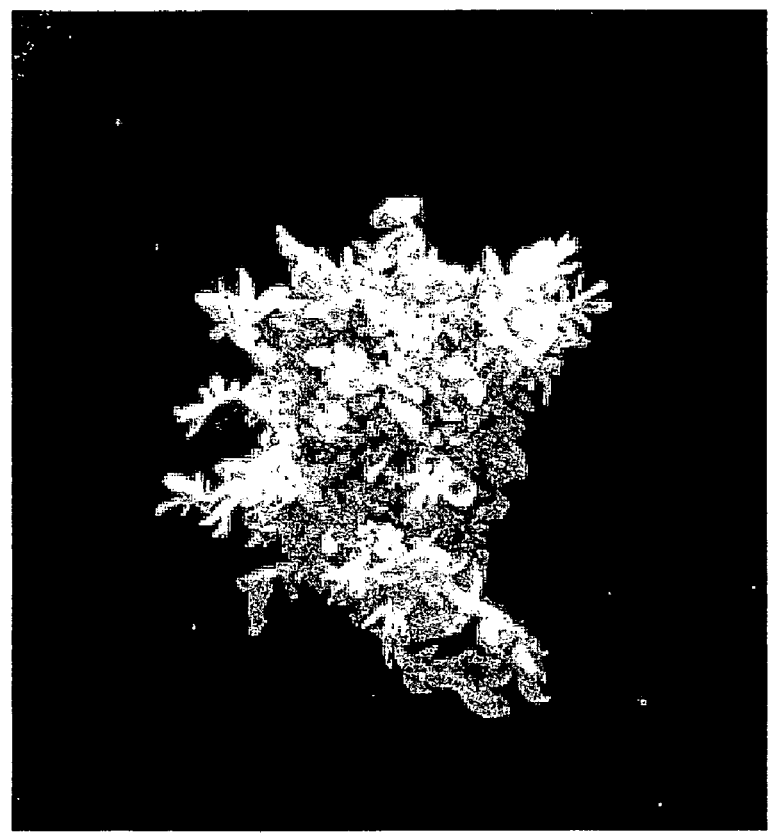
FIG. 6A shows adventitious buds and FIG. 6B shows stem pieces as explants for transformation.
Figure 6:
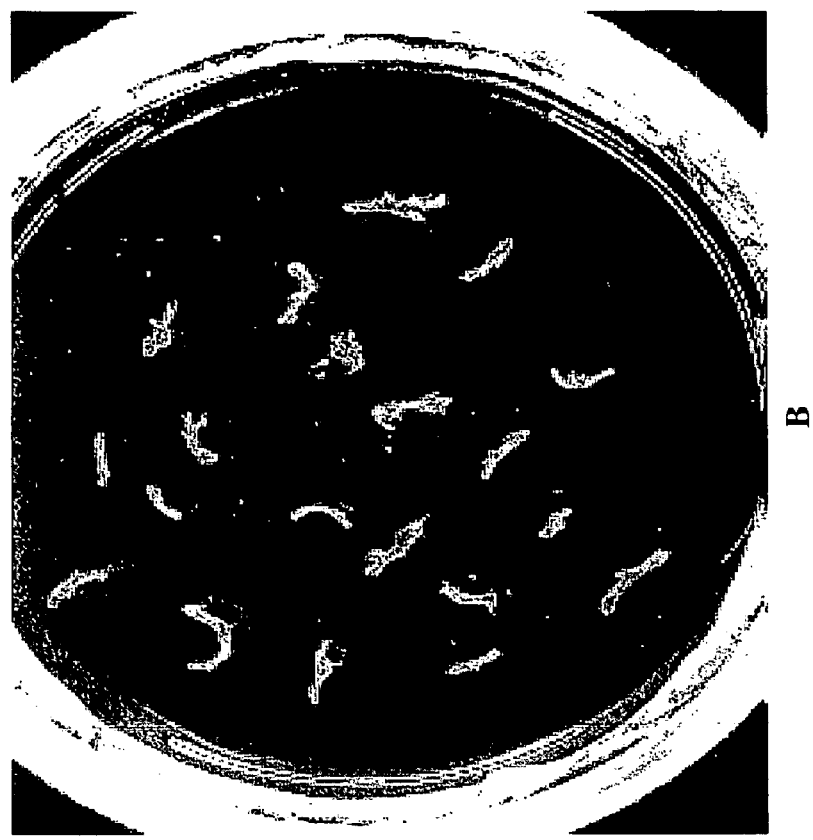

The auxiliary buds of a two-year old young tree (FIG. 5A) were cultured on MS basic medium with NAA 0.1 mg/l, 6-BA 3.0 mg/l, CH 100 mg/l, Vc 100 mg/l, Pro 150 mg/l, Asn 150 mg/l and Gln 150 mg/l, phytagel 0.275% or agar 0.8% (A-4800, Sigma), pH 5.8 after autoclaving at 121° C., sucrose 30 g/L. Sixty days later, some adventitious buds with phyllodes were obtained (FIG. 5B). Induced adventitious buds with phyllodes were subcultured on AM-41 (MS basic medium with 6-BA 2 mg/l, CH 100 mg/l, Vc 100 mg/l, Pro 150 mg/l, Asn 150 mg/l and Gln 150 mg/l, phytagel 0.275% or agar 0.8% (A-4800, Sigma), pH 5.8 after autoclaving at 121° C., sucrose 30 g/L). After sub-culturing adventitious buds with phyllodes twice in about two months, the rejuvenation of adventitious shoots with pinnate leaf was obtained (FIG. 5C). Adventitious buds can be used as explants for transformation (FIG. 6A).

EXAMPLE 6

*A. mangium* Genetic Transformation

A. Activation of *Agrobacterium tumefaciens* Strain LBA4404/pBI21

Figure 4:
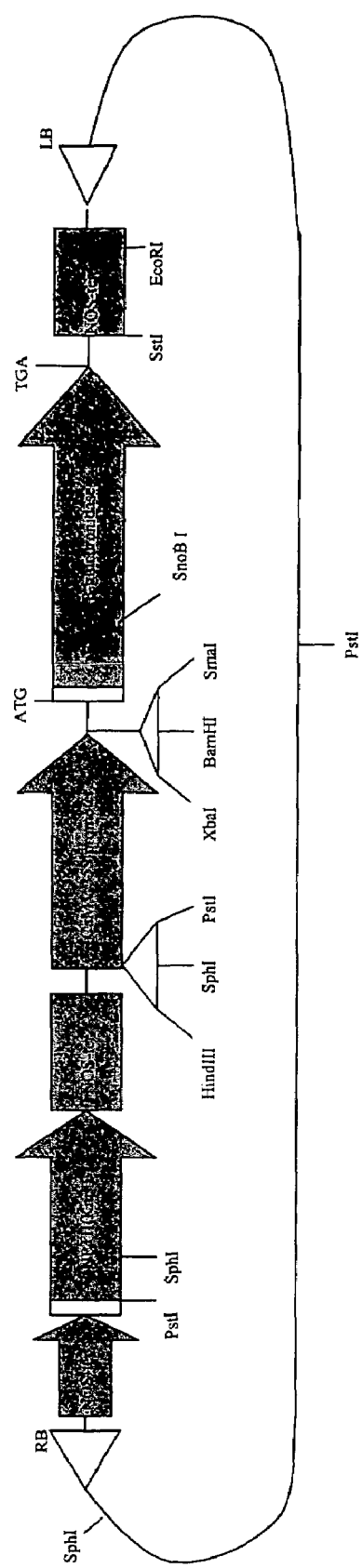
FIG. 4 is a map of pBI121 with an 800 bp HindIII-BamHI fragment containing the cauliflower mosaic virus (CaMV) 35S promoter cloned upstream of the GUS gene.

*Agrobacterium* strain LBA4404 (Ooms et al., 1981) harbouring binary vector plasmid pBI121 (size of vector 13.0 kb, Clontech, FIG. 4) was used for this experiment. pB 121 was derived from pBI101 with an 800-bp HindIII-BamHI fragment containing the cauliflower mosaic virus (CaMV) 35S promoter cloned upstream of the GUS gene. From a permanent glycerol stock stored at −70° C., *Agrobacterium tumefaciens* pBI121/LBA4404 was streaked onto a solid LB (pH 7.0) medium plate containing Streptomycin 100 mg/l ($Str^{100}$) and Kanamycin 50 mg/l ($K^{50}$). This was incubated 2-3 days at 28° C. Fresh pBI121/LBA4404 was streaked onto solid LB medium (pH 7.0) with Streptomycin 100 mg/l ($Str^{100}$) and Kanamycin 50 mg/l ($K^{50}$) for overnight or 24 hours at 28° C. in the dark. Several colonies of pBI121/LBA4404 were picked and pBI121/LBA4404 was inoculated in liquid 50 ml LB medium with Streptomycin 100 mg/l ($Str^{100}$) and Kanamycin 50 mg/l ($K^{50}$), and cultured at 28° C. under dark, 250 rpm for 10 hours until $OD_{600}$=0.70-1.10. This was spun down at 3500 rpm for 30 minutes or 5000 rpm for 10 minutes, and resuspended in 4-5 volumes of YEP medium (pH 7.0) with Streptomycin 100 mg/l ($Str^{100}$) and Kanamycin 50 mg/l ($K^{50}$), $OD_{600}$=0.10-0.20, incubated at 28° C. in the dark, 250 rpm for 8-10 hours, $OD_{600}$=0.70-1.20. This at 3500 rpm for 30 minutes and resuspended in the same volume of sterile NaC 10.9%. This was spun down at 3500 rpm for 30 minutes and resuspended in 2-3.5 volumes of induction medium, $OD_{600}$=0.2-0.3, and incubated at 28° C. in the dark, 120 rpm for 8-15 hours, $OD_{600}$=0.70-1.20 for infecting explants or callus or a cell suspension.

B. Preculture of Stem Pieces

Stem pieces were cultured on AM-265 for 3 days using a photoperiod of 16/8 hrs (L/D), 1800-2000 lux, at 28° C.

C. Co-cultivation

After preculture, stem pieces were soaked in 0.5 M mannitol for 20-25 minutes and then transferred to activated pBI121/LBA4404 suspension for 15 minutes. Infected young stem pieces were washed once and dried on sterile Whatman paper before being cultured on AM-265 with 100 μM acetosyringone at pH 5.2 at 22° C. in the dark for 3 days.

D. Selection of Transformed Adventitious Buds and Transformed Callus

Figure 7:
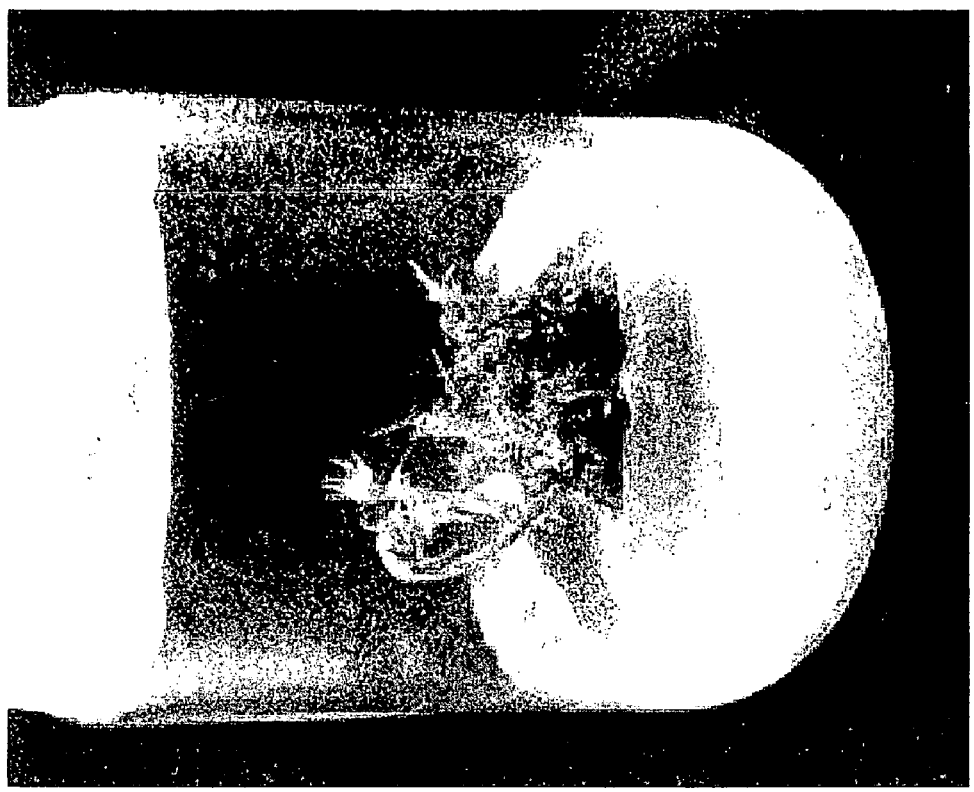
FIG. 7 demonstrates selection and induction of putative transgenic adventitious buds.

After co-culturing for 3 days, stem pieces were washed with sterile $ddH_2O$ for 10 times and dried on sterile Whatman paper. Then stem pieces were cultured on AM-265 containing Timentin 250 mg/l and G418 12 mg/l, phytagel 0.275%, using a photoperiod of 16/8 hrs (L/D) and 28° C. for selecting transformed callus or transformed adventitious buds. Subsequently, stem pieces were cultured on the above media with G418 12 mg/l for 25 days, G418 20 mg/l for 60 days, G418 30 mg/l for 25 days, then on G418 12 mg/l. After continuous selecting for 4 months on antibiotics, 33.75% of stem pieces formed adventitious buds, and 2.5 mg/l to 5 mg/l GA$_3$ was added into the same media to promote adventitious bud elongation (FIG. 7). After selection for five months, Timentin was no longer used in the medium and some adventitious buds were used for GUS staining. GUS staining showed positive blue colour reaction in adventitious buds (FIG. 8, FIG. 9, and FIG. 10). Adventitious buds were transferred to AM-41 with GA$_3$ 2.5 mg/l to promote pinnate leaf formation.

E. Root Formation

Transformed adventitious buds were transferred into AM-357 or AM-451 with or without G418 (10 mg/l) using a photoperiod of 16/8 hrs (L/D) at 28° C.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Ahmad D H (1991). "Micropropagation of *Acacia mangium* from aseptically germinated seedlings" *Journal of Tropical Forest Science* 3(3):204-208.

Anwar C (1992). "The growth of Shorea seedlings on soil media of several age levels of *Acacia mangium* stands" *Buletin Penelitian Hutan* 0(544):9-16.

Awang K (1994). "Growth of three multipurpose tree species on tin tailing in Malaysia" *Journal of Tropical Forest Science* 7(1):106-112.

Basu P K, Ganguly D K, and Mandal G S (1987). "Introduction of exotics in south-west Bengal (India): *Acacia mangium* in coastal area (Digha-Midnapur)" *Indian Forester* 113(10):675-680.

Bayliss M (1998a). *Asia Pacific Papermaker* 8(1):19.

Bayliss M (1998b). *Asia Pacific Papermaker* 8(1):64.

Bhaskan P and Subbash K (1996). "Micropropagation of *Acacia mangium* Willd. through nodal bud culture" *Indian Journal of Experimental Biology* 34:590-591.

Chilton M D, Currier T C, Farrand S K, Bendich A J, Gordon M P and Nester E W (1974). "*Agrobacterium tumefaciens* DNA and PS8 bacteriophage DNA not detected in crown gall tumors" *Proc. Natl. Acad. Sci. USA* 71:3672-3676.

Cole T G, Yost R S, Kablan R and Olsen T (1996). "Growth potential of twelve *Acacia* species on acid soils in Hawaii" *Forest Ecology and Management* 80(1-3):175-186.

Duguma B, Tonye J, Kanmegne J, Manga T and Enoch T (1994). "Growth of ten multipurpose tree species on acid soils in Sangmelima, Cameroon" *Agroforestry Systems* 27(2): 107-119.

Duke J A (1984). "*Acacia mangium* Willd", *Handbook of Energy Crops* (unpublished).

Galiana A, Tibok A and Duhoux E (1991 a). "In Vitro propagation of the nitrogen-fixing tree-legume *Acacia mangium* Willd" *Plant and Soil* 135:151-159.

Galiana A, Tibok A and Duhoux E (1991b). "Nitrogen-fixing potential of micropropagated clones of *Acacia mangium* inoculated with different *Bradyrhizobium* spp. strains" *Plant and Soil* 135(2): 161-166.

Gutteridge R C and Shelton H M (1994). "Forage Tree Legumes" in *Tropical Agriculture* by CAB International.

Jefferson R A (1987). "Assaying chimeric in plants: The GUS gene fusion system" *Plant Mol. Biol. Rep.* 5:387-405.

Khemnark C (1994). "Rehabilitation of degraded tropical forest through agroforestry practices: A case study in Thailand" *Journal of Tropical Forest Science* 7(1): 128-135.

Latif M A, Das S, Rahman M F and Habib M A (1995). "Growth and yield tables for *Acacia mangium* in the plantation in Bangladesh" *Journal of Tropical Forest Science* 7(4):591-598.

Majid N M, Hashim A and Abdol I (1994). "Rehabilitation of ex-tin mining land by agroforestry practice" *Journal of Tropical Forest Science* 7(1):113-127.

Murashige T and Skoog F (1962). "A revised medium for rapid growth and bioassays with tobacco tissue cultures" *Physiol. Plant* 15:473-497.

Ooms G, Hooykaas P J, Moolenaar G and Schilperoort G A (1981). "Grown gall plant tumors of abnormal morphology, induced by *Agrobacterium tumefaciens* carrying mutated octopine Ti plasmids; analysis of T-DNA functions" *Gene* 14:33-50.

Robinson C (1999). "Making forest biotechnology a commercial reality" *Nature Biotechnology* 17: 27-30.

Sambrook J, Fritsch E F and Maniatis T (1989). *Molecular Cloning—A Laboratory Manual* (second edition), Cold Spring Harbor Laboratory Press.

Simmons M H (1987). *Growing Acacias* (edited by Simmons M H) published by Kangaroo Press Pty Ltd.

Tzfira T, Zuker A and Altman A (1998). "Forest-tree biotechnology: genetic transformation and its application to future forests" *TIBTECH* 16:439-446.

Wibowo A, Suharti M and Pickford S G (1992). "Fuel characteristics and fire behaviour in alang-alang under *Acacia mangium* plantation in Depok, West Java" *Buletin Penelitian Hutan* 0(544): 1-7.

Widiarti A and Alrasjid H (1987). "Introduction of fuelwood trees species on degraded lands in Paseh and Kadipaten areas (Indonesia)" *Buletin Penelitian Hutan* 0(488):1-17.

Williams E R, Gunn B, Reynolds D and Westcott M (1992). "Germination tests for small collection of *Acacia* seed" *Seed Science and Technology* 20(2):321-326.

Wong W C, Ho K S and Wong C N (1988). "*Acacia mangium* from Sabah for plywood and decorative panel manufacture: Initial trials" *Journal of Tropical Forest Science* 1(1):42-50.

Yusoff M N M, Chew L T, Ali A R M and Nasir N M (1989). "The adhesive properties of bark extract of *Acacia mangium*" *Journal of Tropical Forest Science* 2(2): 104-109.

What is claimed is:

1. A method of making transgenic *Acacia mangium* plants comprising:
   a) culturing stem pieces of *Acacia mangium* cells on culture medium comprising basic MS medium supplemented with a) thidiazuron, b) indole-3-acetic acid, c) casein enzymatic hydrolysate, d) L-ascorbic acid, e) L-glutamine, f) L-asparagine, g) L-proline, h) sucrose and i) phytagel or agar;
   b) co-cultivating the stem pieces of step (a) with *Agrobacterium* in medium comprising basic MS medium supplemented with a) thidiazuron, b) indole-3-acetic acid, c) casein enzymatic hydrolysate, d) L-ascorbic acid, e) L-glutamine, f) L-asparagine, g) L-proline, h) sucrose, i) acetosyringone and j) phytagel or agar to form infected stem pieces;

c) culturing the infected stem pieces on medium comprising basic MS medium supplemented with a) thidiazuron, b) indole-3-acetic acid, c) casein enzymatic hydrolysate, d) L-ascorbic acid, e) L-glutamine, f) L-asparagine, g) L-proline, h) sucrose, i) an *Agrobacterium* eradicant, j) an antibiotic and k) phytagel or agar to induce and select transformed callus and adventitious bud formation on the stem pieces;

d) culturing the stem pieces having callus and adventitious buds on a medium comprising basic MS medium supplemented with a) thidiazuron, b) indole-3-acetic acid, c) casein enzymatic hydrolysate, d) L-ascorbic acid, e) L-glutamine, f) L-asparagine, g) L-proline, h) sucrose, i) an antibiotic, j) gibberellic acid and k) phytagel or agar to promote adventitious bud elongation;

e) culturing the elongated adventitious buds on medium comprising basic MS medium supplemented with a) 6-benzylaminopurine, b) gibberellic acid, c) casein enzymatic hydrolysate, d) L-ascorbic acid, e) L-glutamine, f) L-asparagine, g) L-proline, h) sucrose, and i) phytagel or agar to promote pinnate leaf formation on the adventitious buds; and f) culturing the adventitious buds with leaves on medium comprising ½ basic MS medium supplemented with a) α-naphthaleneacetic acid, b) kinetin, c) casein enzymatic hydrolysate, d) L-ascorbic acid, e) L-glutamine, f) L-asparagine, g) L-proline, h) sucrose, and i) phytagel to form rooted transgenic plantlets.

2. The method of claim 1 wherein the antibiotic is G418.

3. The method of claim 2 wherein the adventitious buds are cultured for more than 1 month.

4. The method of claim 1 wherein the ½ basic MS medium is further supplemented with an antibiotic.

5. The method of claim 4 wherein the antibiotic is G418.

* * * * *